(12) United States Patent
Lee et al.

(10) Patent No.: US 9,248,320 B2
(45) Date of Patent: Feb. 2, 2016

(54) PERFUME AND COSMETIC COMPOSITION WITH ANTI-STRESS AND RELAXING EFFECT

(75) Inventors: Eun Ju Lee, Suwon-si (KR); Hyung Jye Seo, Yongin-si (KR); Byeong Bae Jeon, Yongin-si (KR)

(73) Assignee: AMOREPACIFIC CORPORATION (KR)

( * ) Notice: Subject to any disclaimer, the term of this patent is extended or adjusted under 35 U.S.C. 154(b) by 148 days.

(21) Appl. No.: 13/257,186

(22) PCT Filed: Mar. 23, 2010

(86) PCT No.: PCT/KR2010/001772
§ 371 (c)(1),
(2), (4) Date: Sep. 16, 2011

(87) PCT Pub. No.: WO2010/110579
PCT Pub. Date: Sep. 30, 2010

(65) Prior Publication Data
US 2012/0015058 A1 Jan. 19, 2012

(30) Foreign Application Priority Data
Mar. 23, 2009 (KR) .......................... 10-2009-0024495

(51) Int. Cl.
| | | |
|---|---|---|
| *A61K 36/752* | (2006.01) | |
| *A61K 36/73* | (2006.01) | |
| *A61K 36/13* | (2006.01) | |
| *A61K 36/282* | (2006.01) | |
| *A61K 36/28* | (2006.01) | |
| *A61Q 13/00* | (2006.01) | |
| *A61K 8/92* | (2006.01) | |
| *A61Q 19/00* | (2006.01) | |

(52) U.S. Cl.
CPC ............... *A61Q 13/00* (2013.01); *A61K 8/922* (2013.01); *A61Q 19/00* (2013.01)

(58) Field of Classification Search
None
See application file for complete search history.

(56) References Cited

U.S. PATENT DOCUMENTS

| | | | | |
|---|---|---|---|---|
| 2004/0033279 A1* | 2/2004 | Warrenburg et al. | .......... | 424/765 |
| 2004/0048771 A1* | 3/2004 | McDermott et al. | .............. | 512/1 |
| 2006/0073211 A1* | 4/2006 | Marenick et al. | .............. | 424/581 |
| 2006/0105005 A1* | 5/2006 | Marenick et al. | .............. | 424/401 |
| 2008/0096790 A1* | 4/2008 | Behan et al. | .................... | 512/27 |

FOREIGN PATENT DOCUMENTS

| | | | |
|---|---|---|---|
| CN | 1969809 A | | 5/2007 |
| CN | 101238204 A | | 8/2008 |
| JP | 04149135 A | * | 5/1992 |
| JP | 04149136 A | * | 5/1992 |
| KR | 20030046949 B1 | * | 6/2003 |
| KR | 10-0465971 B1 | | 1/2005 |
| KR | 10-2005-0097668 A | | 10/2005 |
| KR | 10-2008-0096995 | * | 11/2008 |
| KR | 10-2008-0096995 A | | 11/2008 |
| WO | WO 2005/048964 A1 | | 6/2005 |
| WO | WO2006097759 | * | 9/2006 |
| WO | WO 2007/015481 A1 | | 2/2007 |

OTHER PUBLICATIONS

Komori et al. (1995) Neuroimmunomodulation 2: 174-180.*
Office Action for Chinese Patent Application No. 201080021396.8 (mailed Oct. 19, 2012).

\* cited by examiner

*Primary Examiner* — Chris R Tate
*Assistant Examiner* — Russell Fiebig
(74) *Attorney, Agent, or Firm* — Merchant & Gould P.C.

(57) ABSTRACT

Disclosed is a perfume composition including grapefruit oil and bergamot oil and further including one or more selected from a group consisting of pine oil, lemon oil, cypress oil, rose oil and armoise oil. The perfume composition is useful in the field of beauty care, cosmetics, or the like.

1 Claim, 3 Drawing Sheets

Left brain                Right brain

PERFUME AND COSMETIC COMPOSITION WITH ANTI-STRESS AND RELAXING EFFECT

This application is a U.S. National Stage Application under 35 U.S.C. §371 of International Patent Application No. PCT/KR2010/001772, filed 23 Mar. 2010, which claims the benefit of priority to Korean Patent Application No. KR 10-2009-0024495, filed 23 Mar. 2009 in South Korea, the disclosures of all of which are hereby incorporated by reference in their entireties. The International Application was published in English on 30 Sep. 2010 as WO 2010/110579.

TECHNICAL FIELD

This disclosure relates to a perfume composition and a cosmetic composition with anti-stress and relaxing effects.

BACKGROUND

Stress refers to a state of psychological/physical tension felt under an environment difficult to adapt to. If the stress persists, it may lead to physical diseases such as heart disease, gastric ulcer and hypertension or psychological maladjustments such as insomnia, neurosis and depression. In the industrialized societies filled with conflicts and competitions, most people get a lot of physical/psychological stresses while they try to adapt to the society changing in a complicated way. Moderate stress can be beneficial since it gives an impetus of life and promotes efficiency and productivity. However, since excessive stress may lead to diseases or even death, it is an important health risk factor. Accordingly, to recognize and manage stress well is essential in maintaining and promoting health.

The ways that have been proven effective in treating stress thus far include psychological or mental therapy, biofeedback therapy, progressive relaxation therapy, exercise therapy, or the like. Although the external cause of stress may not directly removed with these methods, they help people appreciate the various stresses occurring incessantly in their lives and get less negative effects on their health. Among these stress-relieving methods, aromatherapy is gradually gathering a lot of attentions. Particularly, use of aroma is increasing to provide a pleasant environment in the workplaces or public places. Especially, it is known that the essential oils used in the aromatherapy relive stress and maintain the balance of autonomic nerves and, thereby, enhances immune functions. According to a subjective evaluation study on the stress and aromatherapy, inhalation of aroma oils resulted in reduced stress in working environments.

DETAILED DESCRIPTION

Technical Problem

This disclosure is directed to providing a perfume composition having an anti-stress effect.

This disclosure is also directed to providing a cosmetic composition having anti-stress and relaxing effects.

Technical Solution

There is provided a perfume composition including grapefruit oil and bergamot oil and further including one or more selected from a group consisting of pine oil, lemon oil, cypress oil, rose oil and armoise oil. There is also provided a cosmetic composition including the perfume composition.

Advantageous Effects

The disclosed perfume composition provides anti-stress and relaxing effects and is usefully applicable in the field of beauty care, cosmetics, and so forth.

BRIEF DESCRIPTION OF THE DRAWINGS

The above and other aspects, features and advantages of the disclosed exemplary embodiments will be more apparent from the following detailed description taken in conjunction with the accompanying drawings in which.

BEST MODE

Figure 1:
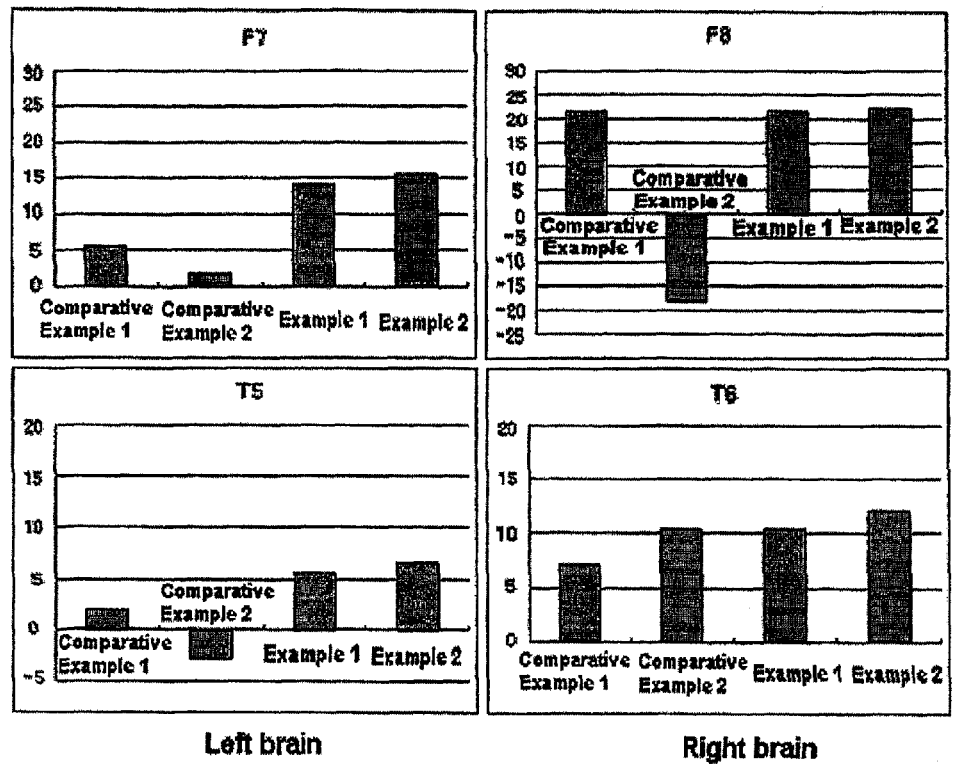
FIG. 1 shows a result of monitoring brainwaves after use of compositions according to an embodiment.

Exemplary embodiments now will be described more fully hereinafter with reference to the accompanying drawings, in which exemplary embodiments are shown. This disclosure may, however, be embodied in many different forms and should not be construed as limited to the exemplary embodiments set forth therein. Rather, these exemplary embodiments are provided so that this disclosure will be thorough and complete, and will fully convey the scope of this disclosure to those skilled in the art. In the description, details of well-known features and techniques may be omitted to avoid unnecessarily obscuring the presented embodiments.

The terminology used herein is for the purpose of describing particular embodiments only and is not intended to be limiting of this disclosure. As used herein, the singular forms "a", "an" and "the" are intended to include the plural forms as well, unless the context clearly indicates otherwise. Furthermore, the use of the terms a, an, etc. does not denote a limitation of quantity, but rather denotes the presence of at least one of the referenced item. The use of the terms "first", "second", and the like does not imply any particular order, but they are included to identify individual elements. Moreover, the use of the terms first, second, etc. does not denote any order or importance, but rather the terms first, second, etc. are used to distinguish one element from another. It will be further understood that the terms "comprise" and/or "comprising", or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

This disclosure provides a perfume composition comprising grapefruit oil and bergamot oil and further comprising one or more selected from a group consisting of pine oil, lemon oil, cypress oil, rose oil and armoise oil. There is also provided a cosmetic composition including the perfume composition.

The grapefruit is the fruit of a grapefruit citrus tree. The grapefruit oil is a yellow oil with a fresh fragrance, and is known to be effective in promoting blood circulation, making people feel pleasant, improving confidence, relieving stress, or the like. The grapefruit oil is a citrus oil containing the monoterpene hydrocarbon limonene as main component. It contains limonene with a content of about 90% and also contains small amounts of terpene and decanol. Besides, it contains small amounts of cadinene, neral, citronellal, or the like.

The bergamot is an evergreen shrub belonging to Family Rutaceae, Order Geraniales, Subclass Archchlamydeae of Class Dicotyledoneae. It is grown in Europe to obtain fragrance and essential oil, and is also planted as an ornament. The bergamot oil refers to the fragrance oil obtained from the outer skin of the bergamot fruit. It contains limonene and linalyl acetate with a content of 40% or more and also contains linalool and bergamotene as a characteristic ingredient. The bergamot oil is a colorless citrus oil with a fresh and pungent fragrance. It is effective in stabilizing the mind, aiding respiration, and relaxing tense muscles.

The pine oil is a term collectively referring to the oil extracted from pine needles and is also called the pine needle fragrance oil. For example, it may be extracted through steam distillation of the pine needles.

The lemon oil is a term collectively referring to the oil extracted from lemon. The lemon oil may be extracted from, for example, the peel of the lemon fruit.

The cypress oil refers to an essential oil of the cypress tree of the family Cupressaceae. It is known to have relaxing and brain freshening effects.

The rose oil is a term collectively referring to the essential oil extracted from rose. With a deep and strong scent, it is effective in relaxing tense mind and body, and relieving fatigue and stress.

And, the armoise oil is a colorless or pale yellow liquid with an odor of mugwort. It is known to effective in treating cramps, strengthening the womb and the bladder, and relaxing the nerves.

In an embodiment, the grapefruit oil may be comprised in an amount of 30 to 70 wt % based on the total weight of the perfume composition and the bergamot oil may be comprised in an amount of 10 to 30 wt % based on the total weight of the perfume composition. The aforesaid ranges are selected as optimum ranges for relieving stress and providing good preference.

In an embodiment, the one or more selected from the group consisting of pine oil, lemon oil, cypress oil, rose oil and armoise oil may be comprised in an amount of 0.1 to 50 wt %, more specifically 15 to 35 wt %, based on the total weight of the perfume composition. In an embodiment, the pine oil may be comprised in an amount of 1 to 20 wt %, the lemon oil may be comprised in an amount of 1 to 20 wt %, the cypress oil may be comprised in an amount of 1 to 20 wt %, the rose oil may be comprised in an amount of 0.1 to 5 wt % and the armoise oil may be comprised in an amount of 0.1 to 5 wt %, based on the total weight of the perfume composition. With contents below the aforesaid ranges, a sufficient effect may not be attained. And, at contents above the aforesaid ranges, the scent of a particular oil may be too strong and, thus, preference may degraded.

In an embodiment, the perfume composition may be a composition for relieving stress or relaxing mind and body. The grapefruit oil and the bergamot oil have the effect of stabilizing and relaxing mind and body, and the other essential oils further improve the stress relieving effect and provide good preference.

This disclosure further provides a cosmetic composition comprising the perfume composition. Specific formulations of the cosmetic composition are not particularly limited. For example, it may be prepared into softening lotion, astringent lotion, nourishing lotion, nourishing essence, nourishing cream, massage cream, essence, eye cream, eye essence, cleansing cream, cleansing foam, cleansing water, pack, gel, powder, makeup base, body lotion, body cream, body oil, body essence, or the like. Further, it may be prepared into transdermal formulations such as lotion, ointment, gel, cream, patch and spray.

The cosmetic composition may comprise the perfume composition in an amount of 0.001 to 10 wt %, specifically 0.1 to 1.0 wt %, based on the total weight of the cosmetic composition. If the perfume composition is comprised in a smaller amount, a desired effect may not be attained. And, if it is comprised in a larger amount, the effect of addition may decrease. The content of the perfume composition may be adjusted within the aforesaid range depending on the characteristic of the particular cosmetic composition.

In an embodiment, the cosmetic composition may further comprise *Helichrysum* extract. In an embodiment, the *Helichrysum* extract may be comprised in an amount of 0.001 to 1.0 wt %, specifically 0.01 to 0.5 wt %, based on the total weight of the cosmetic composition. The addition amount of the *Helichrysum* extract may be adequately selected within a range providing improved stress relieving effect without harming preference.

The *Helichrysum* extract refers to an extract of an annual or biennial grass of the family Asteraceae. Traditionally, the *Helichrysum* extract has been processed as tea or oil and used to treat skin disease, asthma, bronchitis, arthritis, dyspepsia, headache, or the like. It is also used to expel parasitic worms from the body. Recently, it was reported to have superior antibacterial and antiinflammatory effects and be effective in promoting formation of collagens, which are involved in skin elasticity and aging, and proliferation of fibroblasts.

The cosmetic composition may be a composition for relieving stress or relaxing mind and body. By using the perfume composition containing grapefruit oil and bergamot oil, which have anti-stress and relaxing effects, together with the *Helichrysum* extract, which is commonly used to treat depression, neuralgia and stress-related diseases, the effect of relieving stress and relaxing mind and body may be expected.

The perfume composition or the *Helichrysum* extract may be mixed in formulations for skin external application such as perfumes and cosmetics. The addition amount may be adequately determined by those skilled in the art to attain a desired effect. The formulations for skin external application are not particularly limited in form. Examples include ointment, lotion, solution, suspension, emulsion, cream, gel, spray, puff, plaster, patch, pain-relieving medication, or the like.

MODE FOR INVENTION

The examples and experiments will now be described. The following examples and experiments are for illustrative purposes only and not intended to limit the scope of this disclosure.

EXAMPLE 1

Preparation of Perfume Composition

A perfume composition was prepared as given in Table 1.

TABLE 1

| Ingredients | Contents (wt %) |
|---|---|
| Grapefruit oil | 50 |
| Bergamot oil | 20 |
| Pine oil | 10 |
| Lemon oil | 5 |
| Cypress oil | 5 |
| Rose oil | 5 |
| Armoise oil | 5 |
| Total | 100 |

TEST EXAMPLE 1

Measurement of Physiological/Psychological Effects of Perfume Composition

For the perfume composition prepared in Example 1, physiological signals including alpha wave in the electroencephalogram (EEG) of the central nervous system, mean pulse interval (mean R-R interval) the autonomic nervous system, skin temperature and skin conductance were measured. Details are as follows.

1. Test Subjects

Test was carried out on twenty healthy women in their 20s and 30s, who were not taking drugs and not anosmic. They were asked to avoid severe exercise or excessive drinking on the day before the test. They were also asked to avoid smoking or taking beverages, drugs or gums, which may affect the central nervous system and the olfactory sense, on the test day. Menstrual period of the test subjects was considered because it is reported that women's olfactory sense and mood are related with the menstrual period.

2. Test Samples

Test samples were the perfume composition of Example 1 (Table 1) and grapefruit oil (Comparative Example 1, specific gravity: 0.845-0.865, refractive index: 1.471-1.481) and bergamot oil (Comparative Example 2, specific gravity: 0.862-0.882, refractive index: 1.455-1.475) for comparison. Control sample contained no perfume at all.

3. Test Condition

Test was performed in an olfactory laboratory (4.8 m 3 m 2.4 m), with facilities for ventilation installed to reduce olfactory adaptation. The laboratory was also designed to be soundproof in order to maximize the subjects participation in the test and eliminate effect from the external environment during the test. The laboratory condition was maintained constant at temperature 25° C., humidity 40-50% and brightness 150-200 lx. After a test for one condition, the subject was allowed to take enough rest in order to eliminate effect from the previous test. The next test was carried out after ventilating the laboratory.

4. Test Procedure

Sensors to detect brainwaves and physiological signals were attached to the subject before a test. After allowing 2 minutes for relaxation, the subject was asked to close eyes and the sample was provided for 1 minute at a distance of 1-2 cm from the nose. For each subject, the samples were provided at random order, in order to avoid any order effect. The three samples containing perfume were provided by dropping on clean, uncontaminated cotton held in a brown bottle in 1 mL aliquots using a micropipette (Socorex, Switzerland). Physiological responses were measured while the subject smelled the sample and, after the test, the subject was asked to answer a questionnaire about subjective feeling.

5. Measurement Method

Brainwaves were measured using MP 100 system (Biopac, USA) and AcqKnowledge software (Biopac, USA) after attaching electrodes for brainwave measurement (Grass, USA) over the frontal, parietal, temporal and occipital lobes according to the International 10-20 system. Electrical resistance at each measurement location was 10 k or lower and sampling rate was set at 512 Hz.

Physiological signal measurement was made as follows. Electrocardiogram (ECG, CM5) was monitored after attaching ECG electrodes on the chest. Skin temperature and skin conductance (galvanic skin response) were measured by attaching sensors on the left little finger and on the left middle and ring fingers, respectively. For the physiological signal measurement, MP 100 system and AcqKnowledge software were used. Sampling rate was set at 512 Hz. Subjective feeling was evaluated using a translated Profile of Mood States (POMS: Japanese edition, 65 questions). The mood was evaluated as tense, depressed, angry, vigor, fatigued or confused.

6. Analysis Method

Brainwaves transformed into power spectrum values using a fast Fourier transform (FFT) method. $a/(a+\beta+0+d)$ and $\beta/(a+\beta+0+d)$ were calculated depending on frequency ranges. The monitored brainwaves were mapped using a brainwave mapping software (BrainMap 3D, Neuromedi, Korea). Hear rate variability (HRV) was calculated from the mean R-R interval of the R points detected in the ECG. Low frequency (LF: 0.04-0.08 Hz) and high frequency (HF: 0.15-0.4 Hz) values were calculated from the power spectrum. Skin temperature and skin conductance were obtained from the mean amplitude of corresponding waveforms. Each physiological signal was normalized with respect to the perfume-free condition. Mean and standard deviation values were calculated for the physiological signals and emotional and subjective feelings. Statistical analysis was made using analysis of variance (ANOVA) and t-test, using SPSS software.

7. Test Result 7.1. Brainwave Measurement Result

The alpha wave measurement result is shown in FIG. 1. The activity of alpha wave for different samples was compared. Comparative Example 1 and Example 1 showed higher activity of the alpha wave. The alpha wave activity was higher in the right brain than in the left brain. In particular, the perfume composition of Example 1 resulted in increased alpha wave activity in the whole region. The fact that alpha wave activity is higher in the right brain than in the left brain means that the subject feels that the fragrance pleasantly. The perfume providing high alpha wave activity provides relaxation and comfort to the human body.

7.2. Physiological Signal Measurement Result

Figure 2:
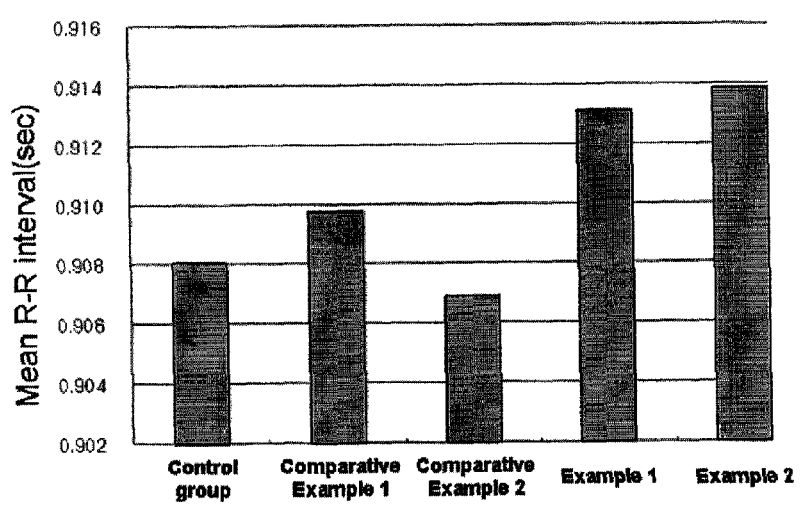
FIG. 2 shows a result of measuring hear rate variability after use of compositions according to an embodiment.
Figure 3:
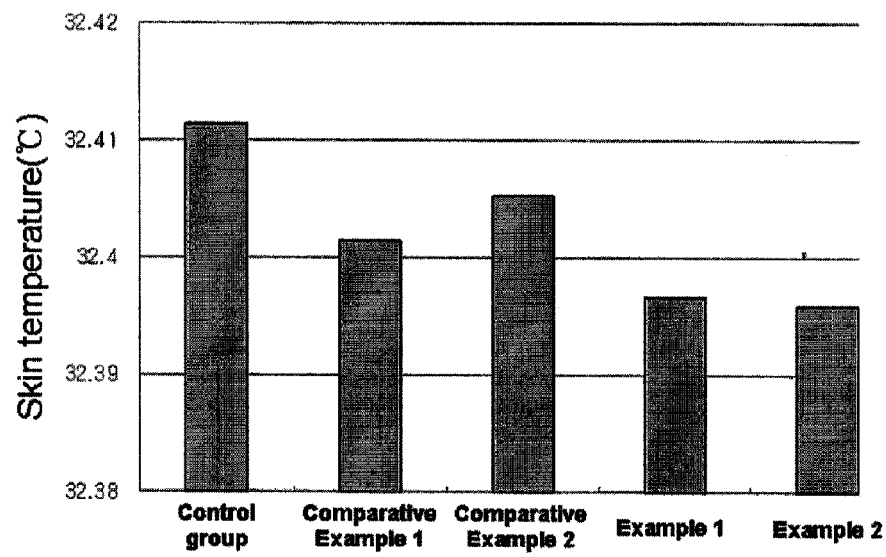
FIG. 3 shows a result of measuring skin temperature after use of compositions according to an embodiment.
Figure 4:
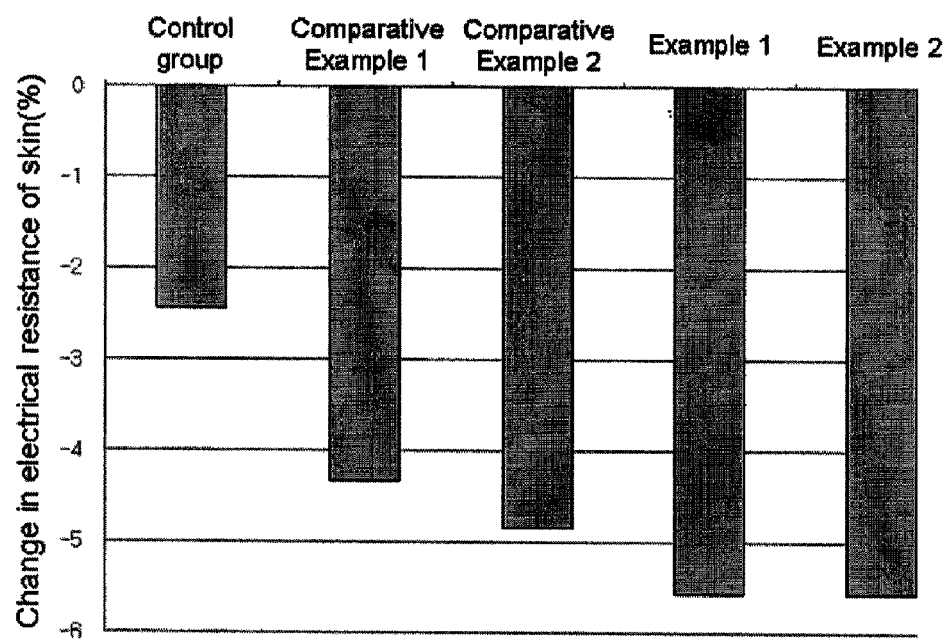
FIG. 4 shows a result of measuring skin conductance after use of compositions according to an embodiment.

Hear rate variability (mean R-R interval), skin temperature and skin conductance measurement results are given in FIGS. 2 to 4.

Comparison of the response of autonomic nerves to different fragrances (see FIG. 2), revealed that mean R-R interval was higher in Comparative Example 1 and Example 1 as compared to the control group. Especially, Example 1 exhibited a large mean R-R interval. A large mean R-R interval indicates that the heart is beating slowly, which means that the subject is feeling comfortable and stabilized.

Comparative Example and Example 1 also showed lower skin temperature (see FIG. 3) and electrical resistance of skin (see FIG. 4) as compared to the control group. Especially, Example 1 showed the best result. Low skin temperature and electrical resistance indicate that the physiological activities are settled and the subject is feeling comfortable and stabilized.

7.3. Subjective Feeling

Figure 5:
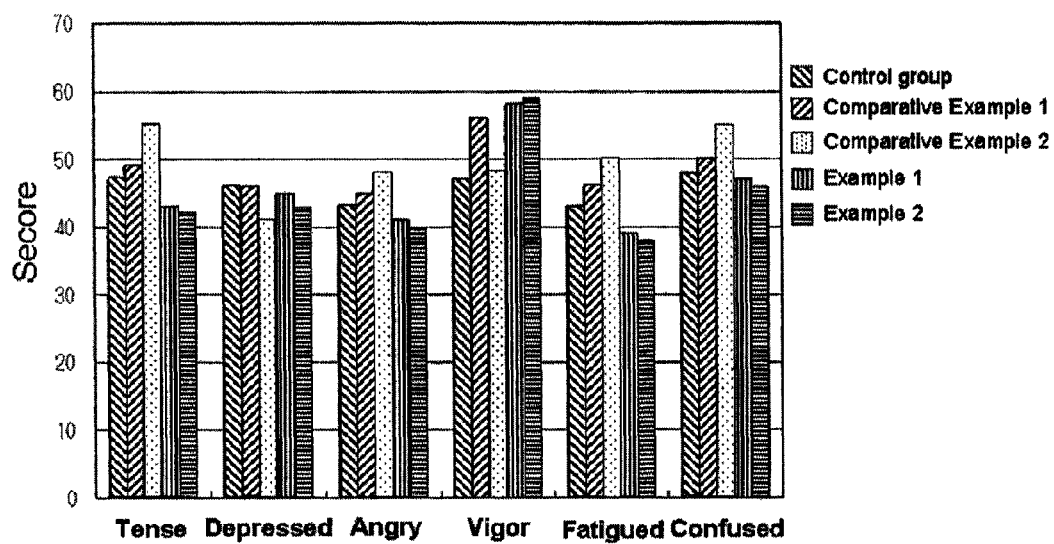
FIG. 5 shows a result of evaluating subjective feeling after use of compositions according to an embodiment.

The evaluation result of subjective feeling is shown in FIG. 5. The subjects were asked to report subjective feelings after providing the three samples. The perfume composition of Example 1 resulted in significantly lower points in tense, angry, fatigued and confused, as compared to control group, Comparative Example 1 and Comparative Example 2. Thus, it can be seen that the perfume composition of Example 1 provides anti-stress and relaxing effects.

EXAMPLE 2

Preparation of Cosmetic Composition Including *Helichrysum* Extract

A cosmetic composition comprising the perfume composition of Example 1 and *Helichrysum* extract as effective ingredients were prepared in the form of essence as given in Table 2.

TABLE 2

| Ingredients | Contents (wt %) |
|---|---|
| Cetearyl alcohol/cetearyl glucoside | 2.0 |
| Polygryceryl-10 stearate | 1.1 |
| Plant-derived squalane | 3.0 |
| Butylene glycol dicaprylate/dicaprate | 0.5 |
| Trioctyldodecyl citrate | 0.6 |
| Dimethicone | 2.2 |
| Cyclopentasiloxane | 3.0 |
| Purified water | 66.47 |
| Disodium EDTA | 0.02 |
| Betaine | 1.2 |
| Glycereth-26 | 1.8 |
| Butylene glycol | 6.0 |
| Glycerine | 1.3 |
| Xanthan gum | 0.05 |
| Hydroxyethyl acrylate/sodium acryloyl dimethyl taurate copolymer | 0.3 |
| Ethanol | 3.0 |
| Perfume composition of Example 1 | 0.1 |
| *Helichrysum* extract | 0.01 |
| Phenoxyethanol | 0.3 |
| Ethylhexylglycerine | 0.05 |
| Butylene glycol | 7.0 |
| Total | 100.0 |

TEST EXAMPLE 2

Measurement of Physiological/Psychological Effects of Cosmetic Composition Including *Helichrysum* Extract Test was carried out to objectively evaluate physiological/psychological effects of the cosmetic composition further comprising the *Helichrysum* extract. Test subjects, test condition, test method and analysis method were the same as Test Example 1, but test samples and test procedure were different.

1. Test Subjects

Test was performed on the same subjects as in Test Example 1.

2. Test Samples

*Helichrysum* extract was prepared by extracting *Helichrysum*, an annual or biennial grass of the family Asteraceae, through steam distillation or water or solvent extraction. The cosmetic composition of Example 2 was used to investigate a synergic effect resulting from addition of the *Helichrysum* extract.

3. Test Condition

Test condition was the same as in Test Example 1.

4. Test Procedure

Sensors to detect brainwaves and physiological signals were attached to the subject before a test. After allowing 2 minutes for relaxation, the cosmetic composition of Example 2 was directly applied on the face of the subject and physiological responses were measured. After the test, the subject was asked to answer a questionnaire about subjective feeling.

5. Measurement Method

Measurement method was the same as in Test Example 1.

6. Analysis Method

Analysis method was the same as in Test Example 1.

7. Test Result 7.1. Brainwave Measurement Result

The alpha wave measurement result is shown in FIG. 1 along with the result of Test Example 1.

The activity of alpha wave for different samples was compared. Example 2 showed higher activity of the alpha wave than Example 1. The alpha wave activity was higher in the right brain than in the left brain. The high activity of alpha wave means that the subject feels relaxed and comfortable. The higher activity in Example 2 reveals that the effect was further increased by the addition of the *Helichrysum* extract.

7.2. Physiological Signal Measurement Result

Physiological signals such as mean R-R interval, skin temperature and skin conductance measurement were measured in the same manner as Example 1. The results are given in FIGS. 2 to 4.

Mean R-R interval was larger in Example 2 than in Example 1. A large mean R-R interval indicates that the heart is beating slowly, which means that the subject is feeling comfortable and stabilized.

Example 2 also showed lower skin temperature and electrical resistance than Example 1. Low skin temperature and electrical resistance indicate that the physiological activities are settled and the subject is feeling comfortable and stabilized. Thus, it can be seen that the contents of Example 2 provide better comfort and sense of stability than those of Example 1.

7.3. Subjective Feeling

The evaluation result of subjective feeling is shown in FIG. 5. The subjects were asked to report subjective feelings after providing the cosmetic composition including the perfume composition and the *Helichrysum* extract. The cosmetic composition of Example 2 resulted in significantly lower points in tense, angry, fatigued and confused, as compared to control group, Comparative Example 1, Comparative Example 2 and the perfume composition of Example 1. Thus, it can be seen that the cosmetic composition of Example 2 provides better subjective feeling.

A variety of cosmetic formulations were prepared as follows.

FORMULATION EXAMPLE 1

Nourishing Lotion (Milk Lotion)

A nourishing lotion comprising the perfume composition of Example 1 was prepared as follows, according to a commonly used method.

| Ingredients | Contents (wt %) |
| --- | --- |
| Perfume composition of Example 1 | 2.0 |
| Squalane | 5.0 |
| Beeswax | 4.0 |
| Polysorbate 60 | 1.5 |
| Sorbitan sesquioleate | 1.5 |
| Liquid paraffin | 0.5 |
| Caprylic/capric triglyceride | 5.0 |
| Glycerine | 3.0 |
| Butylene glycol | 3.0 |
| Propylene glycol | 3.0 |
| Carboxyvinyl polymer | 0.1 |
| Triethanolamine | 0.2 |
| Antiseptic, pigment, fragrance and *Helichrysum* extract | adequate |
| Purified water | to 100 |

FORMULATION EXAMPLE 2

Softening Lotion (Skin Lotion)

A softening lotion comprising the cosmetic composition of Example 2 was prepared as follows, according to a commonly used method.

| Ingredients | Contents (wt %) |
| --- | --- |
| Cosmetic composition of Example 2 | 2.0 |
| Glycerine | 3.0 |
| Butylene glycol | 2.0 |
| Propylene glycol | 2.0 |
| Carboxyvinyl polymer | 0.1 |
| PEG 12 nonyl phenyl ether | 0.2 |
| Polysorbate 80 | 0.4 |
| Ethanol | 10.0 |
| Triethanolamine | 0.1 |
| Antiseptic, pigment, fragrance and *Helichrysum* extract | adequate |
| Purified water | to 100 |

FORMULATION EXAMPLE 3

Nourishing Cream

A nourishing cream comprising the cosmetic composition of Example 2 was prepared as follows, according to a commonly used method.

| Ingredients | Contents (wt %) |
| --- | --- |
| Cosmetic composition of Example 2 | 2.0 |
| Polysorbate 60 | 1.5 |
| Sorbitan sesquioleate | 0.5 |
| PEG60 hydrogenated castor oil | 2.0 |
| Liquid paraffin | 10 |
| Squalane | 5.0 |
| Caprylic/capric triglyceride | 5.0 |
| Glycerine | 5.0 |
| Butylene glycol | 3.0 |
| Propylene glycol | 3.0 |
| Triethanolamine | 0.2 |
| Antiseptic | adequate |
| Pigment | adequate |
| Fragrance and *Helichrysum* extract | adequate |
| Purified water | to 100 |

FORMULATION EXAMPLE 4

Massage Cream

A massage cream comprising the cosmetic composition of Example 2 was prepared as follows, according to a commonly used method.

| Ingredients | Contents (wt %) |
| --- | --- |
| Cosmetic composition of Example 2 | 1.0 |
| Beeswax | 10.0 |
| Polysorbate 60 | 1.5 |
| PEG 60 hydrogenated castor oil | 2.0 |
| Sorbitan sesquioleate | 0.8 |
| Liquid paraffin | 40.0 |
| Squalane | 5.0 |
| Caprylic/capric triglyceride | 4.0 |
| Glycerine | 5.0 |
| Butylene glycol | 3.0 |
| Propylene glycol | 3.0 |
| Triethanolamine | 0.2 |
| Antiseptic, pigment, fragrance and *Helichrysum* extract | adequate |
| Purified water | to 100 |

FORMULATION EXAMPLE 5

Pack

A pack comprising the cosmetic composition of Example 2 was prepared as follows, according to a commonly used method.

| Ingredients | Contents (wt %) |
| --- | --- |
| Cosmetic composition of Example 2 | 1.0 |
| Polyvinyl alcohol | 13.0 |
| Sodium carboxymethylcellulose | 0.2 |
| Glycerine | 5.0 |
| Allantoin | 0.1 |
| Ethanol | 6.0 |
| PEG 12 nonyl phenyl ether | 0.3 |
| Polysorbate 60 | 0.3 |
| Antiseptic, pigment, fragrance and *Helichrysum* extract | adequate |
| Purified water | to 100 |

FORMULATION EXAMPLE 6

Gel

A gel comprising the cosmetic composition of Example 2 was prepared as follows, according to a commonly used method.

| Ingredients | Contents (wt %) |
| --- | --- |
| Cosmetic composition of Example 2 | 2.0 |
| Sodium ethylenediamineacetate | 0.05 |
| Glycerine | 5.0 |
| Carboxyvinyl polymer | 0.3 |
| Ethanol | 5.0 |
| PEG 60 hydrogenated castor oil | 0.5 |
| Triethanolamine | 0.3 |
| Antiseptic, pigment, fragrance and *Helichrysum* extract | adequate |
| Purified water | to 100 |

FORMULATION EXAMPLE 7

Water-in-Oil Emulsion Makeup Base

A water-in-oil emulsion makeup base comprising the cosmetic composition of Example 2 was prepared as follows, according to a commonly used method.

| Ingredients | Contents (wt %) |
| --- | --- |
| Cosmetic composition of Example 2 | 3.0 |
| Butylene glycol | 10 |
| Salt | 1.5 |
| Ozokerite | 2.0 |
| Dicaprylyl carbonate | 20 |
| Sorbitan isostearate | 2.5 |
| Cetyl dimethicone copolyol | 2.0 |
| Poly(methyl methacrylate) | 3.0 |
| Iron oxide | 1.5 |
| Titanium oxide | 12.0 |
| Talc (size: 3.06 μm) | 5.0 |
| Antiseptic, pigment, fragrance and *Helichrysum* extract | adequate |
| Purified water | to 100 |

FORMULATION EXAMPLE 8

Twin Cake Powder

A twin cake powder comprising the cosmetic composition of Example 2 was prepared as follows, according to a commonly used method.

| Ingredients | Contents (wt %) |
| --- | --- |
| Cosmetic composition of Example 2 | 1.0 |
| Nylon powder | 5.0 |
| Modified starch | 3.0 |
| Titanium dioxide | 3.0 |
| Mica | 25.0 |
| Squalene | 0.5 |
| Dimethicone | 0.8 |
| Antiseptic, pigment, fragrance and *Helichrysum* extract | adequate |
| Silicone-treated talc | to 100 |

While the exemplary embodiments have been shown and described, it will be understood by those skilled in the art that various changes in form and details may be made thereto without departing from the spirit and scope of this disclosure as defined by the appended claims. In addition, many modifications can be made to adapt a particular situation or material to the teachings of this disclosure without departing from the essential scope thereof. Therefore, it is intended that this disclosure not be limited to the particular exemplary embodiments disclosed as the best mode contemplated for carrying out this disclosure, but that this disclosure will include all embodiments falling within the scope of the appended claims.

The invention claimed is:

1. A method for relieving stress and/or relaxing mind and body in a subject in need thereof comprising administering to the subject an effective amount of a perfume composition, wherein the perfume composition comprises:
50 wt % grapefruit oil,
20 wt % bergamot oil,
10 wt % pine oil,
5 wt % lemon oil,
5 wt % cypress oil,
0.1 to 5 wt % rose oil,
0.1 to 5 wt % armoise oil, and
0.001 to 1.0 wt % *Helichrysum* extract; based on the total weight of the perfume composition.

* * * * *